United States Patent [19]

Rosasco

[11] Patent Number: 4,670,910

[45] Date of Patent: Jun. 9, 1987

[54] VISOR

[76] Inventor: Leroy P. Rosasco, 906 Lothrop Ave., River Forest, Ill. 60305

[21] Appl. No.: 793,190

[22] Filed: Oct. 31, 1985

[51] Int. Cl.[4] .............................................. A61F 9/00
[52] U.S. Cl. .......................................... 2/177; 2/12; 2/195; 2/209.3
[58] Field of Search ...................... 2/12, 177, 195, 200, 2/171, 209.3

[56] References Cited

U.S. PATENT DOCUMENTS

| | | | |
|---|---|---|---|
| 1,631,210 | 6/1927 | Johnson | 2/12 |
| 2,247,971 | 7/1941 | Snell | 2/12 |
| 2,293,436 | 8/1942 | Kelley | 2/12 |
| 2,521,017 | 9/1950 | Moen et al. | 2/195 X |
| 2,787,791 | 4/1957 | Linney et al. | 2/12 X |
| 2,827,636 | 3/1958 | Hoeflich | 2/195 |
| 2,827,637 | 3/1958 | Wagenfeld | 2/209.3 |

FOREIGN PATENT DOCUMENTS 160103 12/1954 Australia ................................. 2/12

Primary Examiner—Werner H. Schroeder
Assistant Examiner—J. L. Olds
Attorney, Agent, or Firm—Knechtel & Demeur

[57] ABSTRACT

A visor cap formed formed from a single sheet of material such as paperboard including a headband portion and an angularly disposed curved visor and which is particularly adapted for the printing of indicia thereon such as corporate names, logos and the like in a fashion such that the indicia is readily seen by anyone observing the visor.

3 Claims, 4 Drawing Figures

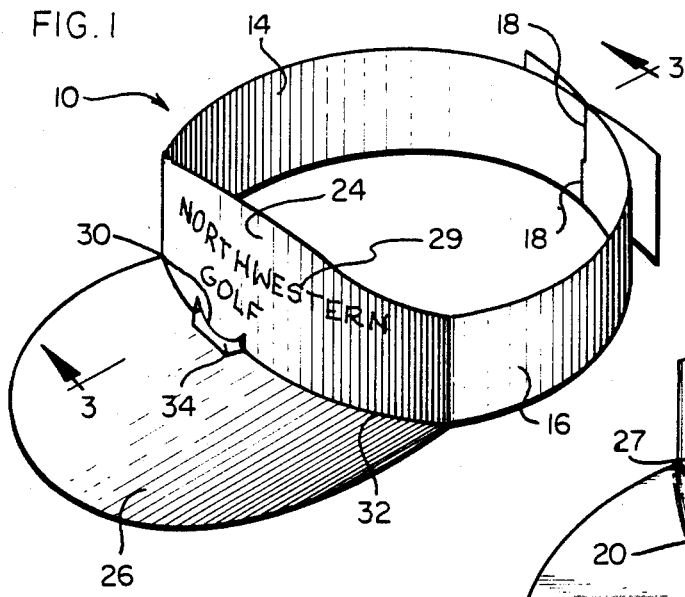
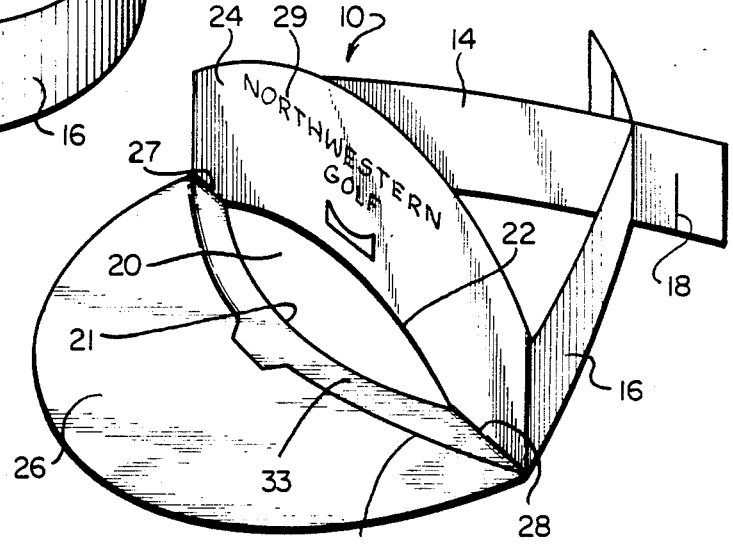
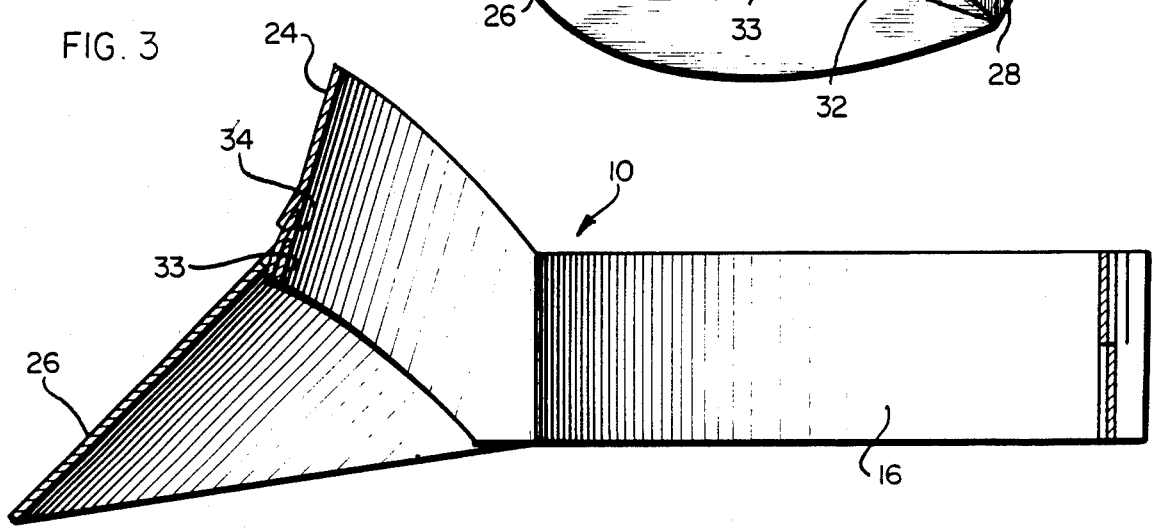
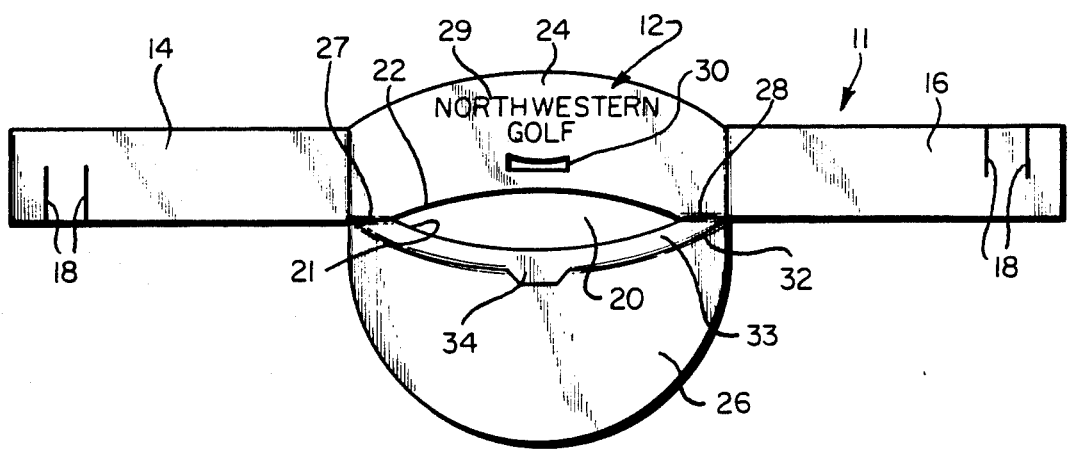

VISOR

BACKGROUND OF THE INVENTION

This invention relates to an improved visor which is made from a single sheet of material such as paperboard and which is particularly adapted for the printing of indicia thereon such as corporate names, logos and the like in a fashion such that the indicia is readily seen by anyone observing the visor.

There are presently a whole host of visors available on the market and many of them are made from a single sheet of material. In most cases these visors simply comprise a visor portion and head band portions which are adapted to encircle the head. Indicia can be printed on the visor portion, but this indicia normally is not readily seen since the visor portion is an angularly disposed curved visor. Accordingly, unless the person wearing the visor has his head tilted downwardly, the indicia is not readily seen.

In many cases these visors are given away at sporting events and the like by various companies who are sponsoring the event. In such cases, these companies print their company's name, logo, or other identifying indicia on the visors for whatever promotional value and recognition they can gain from doing so. This is especially true, for example, at professional golf tournaments which are televised. At such an event, several hundred people may wear these visors. If the advertising indicia on the visors is readily apparent, the company realizes a tremendous amount of exposure which is of considerable value to it for only the cost of the visors. As indicated above, however, with presently available visors, the indicia is not readily seen, hence the value of the visors for advertising purposes is greatly diminished.

Accordingly, it is an object of the present invention to provide an improved visor, particularly one which is adapted to receive indicia thereon in a fashion such that it is readily seen.

Other objects and advantages of the visor of the present invention will be apparent from the following drawings and description, wherein:

FIG. 1 is a perspective view of the visor;

FIG. 2 is a perspective view of the visor partially folded or assembled;

FIG. 3 is a sectional view of the visor taken along lines 3—3 of FIG. 1; and

FIG. 4 is a top plan view of the cut and scored sheet of material from which the visor is formed.

DESCRIPTION OF A PREFERRED EMBODIMENT

Referring now to the drawing, there is illustrated a visor 10 which is formed integrally from a single sheet of material such as paperboard or the like which is cut and scored to form a center portion 12 from which extends head band portions 14 and 16. The head band portions 14 and 16 have slits 18 formed in them which can be interlocked as shown in FIGS. 1-3 to provide an adjustable fit to a person's head size. The center portion 12 and the head band portions 14, 16 obviously are adapted to encircle a person's head.

The center portion 12 has a cut-out 20 formed in it which is defined by upper and lower horizontally extending arcuate lines 21 and 22 which merge together or join one another at the terminal ends thereof. The cut-out 20 generally defines on the center portion 12 an upper panel portion 24 and a lower visor portion 26.

The upper panel portion 24 and the lower visor portion 26 are further defined by a pair of horizontal scored lines 27 and 28 which are in horizontal alignment with one another and which extend from the cut-out 20 and intersect and merge with an arcuate scored line 32 on the visor portion 26. The upper panel portion 24 also has indicia 29, such as a corporate name, logo, or the like, printed on it, and when the visor 10 is folded as described below, and worn, the upper panel portion 24 stands or projects upwardly so that the indicia on it is readily seen. The upper panel portion 24 also has a locking slot 30 formed in it.

The visor portion 26 has an arcuate scored line 32 on it which is spaced from the arcuate line 21 and which is of the same radius as the arcuate line 21, for reasons which will be apparent from the description below. The arcuate line 21 and the arcuate scored line 32 define between them a visor stiffener 33. The visor portion 26 also has a lock tab 34 formed in it which is positioned to lockingly engage with the locking slot 30. It may be noted that one edge of the locking tab 34 is defined by the arcuate scored line 32.

The visors 10 can be printed, stored, and shipped in the flattened position illustrated, hence they can be readily printed and handled. When a visor 10 is to be assembled for use, the visor portion 26 is folded along the score lines 27, 28 against the upper panel portion 24, and the locking tab 34 is lockingly engaged in the locking slot 30. When folded in this fashion, the arcuate lines 21, 22 are in registry with one another and the visor stiffener 33 is effectively lockingly engaged against the upper panel portion 24. Thereafter, the visor portion 26 is creased along the arcuate scored line 32 away from the upper panel portion 24. Now, when the visor 10 is formed to encircle the head, the visor portion 26 forms an arcuately disposed curved visor. More importantly, as can be seen, the upper panel portion 24 stands or projects upwardly from the visor portion 26 when worn by someone so that the indicia 29 on the upper panel portion 24 is readily seen. Of course, indicia also can be affixed to the visor portion 26 and to the head band portions 14, 16 if desired. The locking tab 34 being engaged within the locking slot 30 lockingly engages the visor stiffener 33 against the panel portion 24 to both stiffen the visor 10 and to prevent the visor portion 26 from unfolding such that, once assembled, the visor 10 retains its shape.

What is claimed is:

1. A visor cap formed integrally from a single sheet of material which is cut out and scored to form a center section having opposite sides, a head band portion extending from each of the opposite sides of said center section, said center section and said head band portions being adapted to encircle the head, said center section including a cut-out therein defined by an upper and a lower horizontally extending arcuate line which have terminal ends that join one another, said cut-out generally defining on said center section an upper panel portion and a lower visor portion, said upper panel portion having a locking slot formed therein, said lower visor portion having an arcuate scored line formed on it which has terminal ends and a radius corresponding to the radius of and which is in spaced relationship to said lower horizontally extending arcuate line, said lower visor portion further having a locking tab formed on it which has one edge thereof defined by said arcuate scored line, a pair of horizontal scored lines extending between said cut-out and the respective terminal ends of said arcuate scored line, said visor being folded against said upper panel portion along said pair of horizontal scored lines and said locking tab being disposed within said locking slot in said upper panel portion to removably secure said visor portion and said upper panel portion together, said visor portion being folded along said arcuate scored line so as to cause the visor to form an angularly disposed curved visor.

2. The visor cap of claim 1, wherein said lower horizontally extending arcuate line and said arcuate scored line define between them a visor stiffener, said visor stiffener being secured against said upper panel portion when said visor cap is assembled to both stiffen and to prevent said visor cap from unfolding.

3. The visor cap of claim 1, wherein said single sheet of material comprises paperboard.

* * * * *